United States Patent
Mark et al.

(10) Patent No.: US 12,414,791 B2
(45) Date of Patent: Sep. 16, 2025

(54) FLEXIBLE INSTRUMENT DELIVERY DEVICE

(71) Applicant: Stryker Corporation, Portage, MI (US)

(72) Inventors: Joseph L. Mark, Indianapolis, IN (US); Brian C. Dougherty, Terre Haute, IN (US); Inder Jarial, Carmel, IN (US); Ethan Elijah Mahn, Centerburg, OH (US)

(73) Assignee: Stryker Corporation, Portage, MI (US)

( * ) Notice: Subject to any disclaimer, the term of this patent is extended or adjusted under 35 U.S.C. 154(b) by 464 days.

(21) Appl. No.: 17/858,740

(22) Filed: Jul. 6, 2022

(65) Prior Publication Data
US 2023/0011661 A1    Jan. 12, 2023

Related U.S. Application Data

(60) Provisional application No. 63/219,085, filed on Jul. 7, 2021.

(51) Int. Cl.
*A61B 17/32* (2006.01)
*A61B 17/34* (2006.01)

(52) U.S. Cl.
CPC .... *A61B 17/32002* (2013.01); *A61B 17/3421* (2013.01); *A61B 17/3423* (2013.01)

(58) Field of Classification Search
CPC .......... A61B 17/32002; A61B 17/3421; A61B 17/3423; A61B 1/00154; A61B 1/0125; A61B 1/3132; A61B 1/012
See application file for complete search history.

(56) References Cited

U.S. PATENT DOCUMENTS

| | | |
|---|---|---|
| 9,345,386 B1 | 5/2016 | Cheng |
| 10,085,649 B1 | 10/2018 | Valko et al. |
| 10,105,042 B2 | 10/2018 | Davis et al. |
| 10,172,514 B2 | 1/2019 | Davis et al. |
| 10,172,525 B2 | 1/2019 | Davis et al. |
| 10,376,281 B2 | 8/2019 | Davis et al. |
| 10,398,318 B2 | 9/2019 | Davis et al. |
| 10,413,169 B2 | 9/2019 | Davis et al. |
| 10,544,974 B2 | 1/2020 | Goldfarbmuren et al. |
| 10,555,666 B2 | 2/2020 | Davis et al. |
| 10,646,212 B2 | 5/2020 | Chhit et al. |
| 10,722,265 B1 | 7/2020 | Davis |
| 10,874,303 B2 | 12/2020 | Tsukashima et al. |
| 11,185,218 B2 | 11/2021 | Davis et al. |
| 11,376,039 B2 | 7/2022 | Seifert et al. |
| 11,529,168 B2 | 12/2022 | Tsukashima et al. |
| 2004/0102804 A1 | 5/2004 | Chin |

(Continued)

FOREIGN PATENT DOCUMENTS

WO    2012083245 A1    6/2012

*Primary Examiner* — Richard G Louis
(74) *Attorney, Agent, or Firm* — Howard & Howard Attorneys PLLC (57) ABSTRACT

A surgical access assembly may include an outer sheath defined by an open distal end and an open proximal end and including a hollow body portion therebetween, and a flexible tool delivery device having a hub and a guide tube, the hub configured to selectively secure to a rim at the proximal end of the outer sheath, and the guide tube configured to extend at least partially into the outer sheath and provide a flexible tool proximate to a tissue.

22 Claims, 11 Drawing Sheets

(56) References Cited

U.S. PATENT DOCUMENTS

| | | | |
|---|---|---|---|
| 2004/0167559 A1* | 8/2004 | Taylor | A61B 17/3462 606/185 |
| 2006/0063973 A1 | 3/2006 | Makower et al. | |
| 2008/0319387 A1 | 12/2008 | Amisar et al. | |
| 2014/0074126 A1* | 3/2014 | Voss | A61B 17/0482 606/148 |
| 2020/0179078 A1 | 6/2020 | Tsukashima et al. | |
| 2020/0253464 A1 | 8/2020 | Flower et al. | |
| 2020/0268243 A1 | 8/2020 | Davis et al. | |
| 2021/0052300 A1 | 2/2021 | Fuller | |

\* cited by examiner

FLEXIBLE INSTRUMENT DELIVERY DEVICE

CROSS-REFERENCE TO RELATED APPLICATIONS

This application claims the benefit of U.S. provisional application Ser. No. 63/219,085, filed Jul. 7, 2021, the disclosure of which is hereby incorporated in its entirety by reference herein.

TECHNICAL FIELD

The present disclosure relates generally to a surgical access system for use with delicate and critical tissues, as well as methods of accessing and performing surgery using same. More specifically, the present disclosure relates to a flexible instrument delivery device for delivering tools, such as an imaging device to the tissues.

BACKGROUND

Diagnosis and treatment of conditions affecting the human body, and specifically the brain, are among the most difficult and complex problems that face the medical profession. The brain is a complex and delicate soft multi-component tissue structure that controls bodily functions through a complex neural network connected to the rest of the body through the spinal cord. The brain and spinal cord are contained within and protected by significant bony structures, e.g., the skull and the spine. Given the difficulty of accessing the brain through the hard bony protective skull and the delicate network and complex interactions that form the neural communication network contained within the brain that define the human body's ability to carry on its functions of speech, sight, hearing, functional mobility, reasoning, emotions, respiration and other metabolic functions, the diagnosis and treatment of brain disorders presents unique challenges not encountered elsewhere in the body.

For example, abnormalities such as intracranial cerebral hematomas (ICH), abscesses, glioblastomas (GB), metastases (mets) and functional diseases manifest themselves in the intraparenchymal subcortical space (i.e., the white matter) of the brain are particularly challenging to access, let alone treat. The ventricles of the brain contain eloquent communication structures (neural network) which are located in the subcortical space, called fiber tracts and fascicles. Thus, traditionally, unless the ICH, GB, and/or mets were considered anything but "superficial," such conditions have been considered challenging to access, simply because getting to the abnormality ICH, GB and/or mets are considered just as damaging as letting the condition take its course. Similarly, tissue abnormalities such as tumors, cysts and fibrous membrane growths which manifest within the intraventricular space of the brain are considered challenging to safely access and often inoperable, due to their locations within the brain.

In order to assist in diagnosis and subsequent treatment of tissue disorders, clear, accurate imaging of brain tissue through the skull is required. In recent years significant advances have been made in imaging technology, including stereotactic X-ray imaging, Computerized Axial Tomography (CAT), Computerized Tomographic Angiography (CTA), Position Emission Tomography (PET) and Magnetic Resonance Imaging (MM), Diffusion Tensor Imaging (DTI) and Navigation systems (instrument position tracking systems). These imaging devices and techniques permit the surgeon to observe conditions within the brain in a non-invasive manner without opening the skull, as well as provide a map of critical structures surrounding an area of interest, including structures such as blood vessels, membranes, tumor margins, cranial nerves, including fiber tracts and fascicles. If an abnormality is identified through the use of one or more imaging modalities and/or techniques, it may be necessary or desirable to biopsy or remove the abnormality.

SUMMARY

A surgical access assembly may include an outer sheath defined by an open distal end and an open proximal end and including a hollow body portion therebetween, and a flexible tool delivery device having a hub and a guide tube, the hub configured to selectively secure to a rim at the proximal end of the outer sheath, and the guide tube configured to extend at least partially into the outer sheath and provide a flexible tool proximate to a tissue.

A flexible tool delivery device for a surgical system may include a hub configured to selectively secure to a rim at a proximal end of an outer sheath of the surgical system, and a guide tube coupled to the hub and extending at least partially into the outer sheath to provide a flexible tool proximate to a tissue during use.

A surgical access assembly may include an outer sheath defined by an open distal end and an open proximal end and including a hollow body portion therebetween, and a flexible tool delivery device having a hub and a guide tube, the hub configured to selectively secure to a rim at the proximal end of the outer sheath, and the guide tube configured to extend at least partially into the outer sheath and provide a flexible tool proximate to a tissue.

BRIEF DESCRIPTION OF THE DRAWINGS

Exemplary embodiments of the present disclosure will now be described in greater detail with reference to the attached figures, in which.

DETAILED DESCRIPTION

Referring now to the discussion that follows and also to the drawings, illustrative approaches to the disclosed assemblies and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Described herein is a surgical access assembly, various components for use in same, and a method of using the surgical access assembly. The components disclosed herein provide surgeons with an enhanced ability to minimize trauma to the patient, while providing efficient improved minimally invasive surgical techniques, including imaging of the site. In order to acquire images of the site, ancillary light may be provided to the site. This light may be provided by various light sources within the surgical access assembly. The light sources may also be integrated into a camera assembly and delivered to the surgical site via a tube within a sheath.

More specifically, fluorescent markers may be used to help distinguish certain cells within the body tissue. Certain compounds may cause cancerous tissue to become visible, or illuminate, in response to specific light wavelengths being delivered on to the tissue. This may aid in allowing the surgeon to differentiate and identify tissues. The light sources within the surgical access assembly may deliver this light to the site.

Other types of tissue analysis may be delivered and available via the flexible tool delivery device. In on example, spectroscopic analysis of the tissue via laser interrogation at a specific frequency to interrogate the tissue may be delivered via the flexible tool. In this example, the provided laser may bounce off of the tissue and the receiver of the laser console may classify the tissues. Other forms of tissue interrogation may also be provided via the flexible tool delivery device. Further, biopsy or resection devices, as well as light sources, microscopes, other surgical probes, and tools for intercranial, spinal, abdominal procedures, and more.

The surgical access assembly may include a selectively attachable flexible tool delivery device, having the guide tube of the flexible tool delivery device configured to selectively extend within a lumen of the sheath. The flexible tool delivery device may be relatively small, having a much less diameter than that of the sheath so as to not block other tools or cannulas from being arranged or entering the sheath. Further, the flexible tool delivery device is adjustable in that the position of the distal end of the flexible tool relative to the sheath may be axially adjustable by the flexible tool delivery device. The angle at which the flexible tool delivery device is arranged within the sheath is also adjustable and thus allowing different depths and angles of delivery to the surgical site of the flexible tool. The flexible tool delivery device may attach at the proximal end of the sheath and may be pivotable to adjust the angle of the flexible tool.

The position of the flexible tool may be maneuvered via a single thumb movement. The flexible tool may be a camera, but may also be a biopsy device, grasper, or any flexible device, etc. In the example of the camera, the camera may provide the necessary light to the surgical site to illuminate the tissue.

Figure 1:
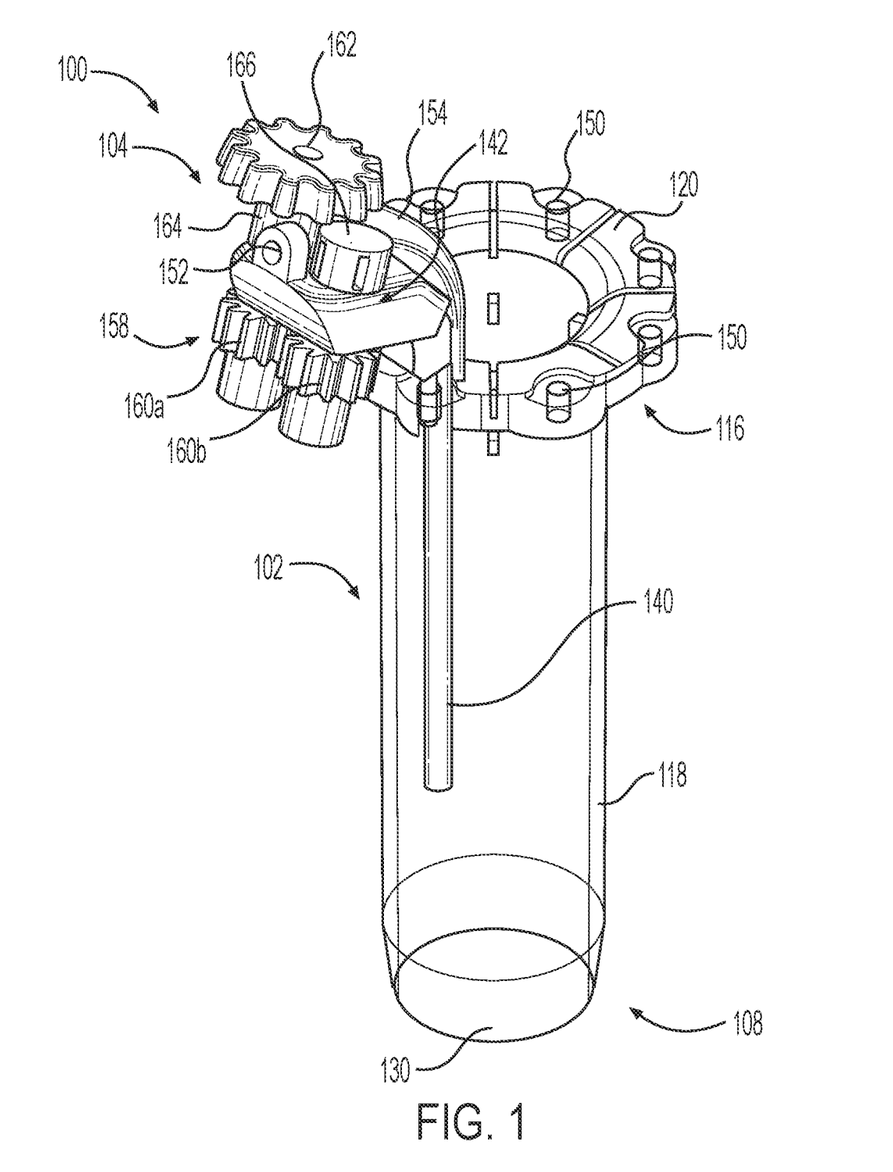
FIG. 1 illustrates a perspective view of a surgical access assembly having a flexible instrument arranged on a hollow outer sheath.

FIG. 1 illustrates a perspective view of a surgical access assembly 100 having a flexible tool delivery device 104 arranged on a hollow outer sheath 102. The outer sheath 102 may be defined by a distal end 108 and a proximal end 116 and include a generally hollow body portion 118. A rim portion 120 is configured as a ring, as illustrated in the drawings. The rim portion 120 may be configured as a grip portion, allowing for engagement by the surgeon. In this example, the rim portion 120 may be referred to as a grip ring and is fixedly secured to body portion 118 at proximal end 116. The outer periphery may further be provided with a textured surface to provide for ease of gripping the outer sheath 102. The rim portion 120 may define a plurality of holes 150.

In one example, the body portion 118 is constructed of a clear biocompatible material that permits viewing of normal tissue, abnormal tissue, as well as critical structures that are disposed outside of body portion 118 when the outer sheath 102 is disposed within such tissue. In one exemplary arrangement, outer sheath 102 is constructed of polycarbonate, though other biocompatible materials may be employed, including resins. The distal end 108 of the outer sheath 102 may include a tapered portion 130. The tapered portion 130 may serve to ease transitions of the sheath 102 into body tissue.

The outer sheath 102 is not intended to be limited to brain tissue applications, but may be a port configured to receive the flexible instrument. In one other example, the sheath 102 may be used for abdominal procedures. The flexible tool delivery device 104 may be configured to selectively attach to the rim portion 120 of the outer sheath 102.

The flexible tool delivery device 104 may be any instrument to be flexibly introduced to or proximate to the tissue via the body portion 118 of the outer sheath 102. In one example, the flexible tool delivery device 104 may be configured to deliver a camera with a filter configured to pick up fluorescent images generated by the tissue. The flexible tool delivery device 104 may include a guide tube 140 extending from a hub 142 into the outer sheath 102, without substantially filling or blocking the lumen of the sheath 102. The guide tube 140 may extend at least partially down three of the sheath 102 within the lumen. The guide tube 140 may be rigid enough to form a generally straight guide within the sheath 102. This is discussed in more detail below.

The flexible tool delivery device 104 includes the hub 142 configured to rest at the rim portion 120. The hub 142 may selectively clamp onto the rim portion 120 via a plurality of mechanisms. In the example shown, the hub 142 may include at least one pin 144. The at least one pin 144 may include a pair of pins arranged on each side of a body 148 of the hub 142. The holes 150 in the rim portion 120 may be configured to receive the at least one pin 144 and secure the flexible tool delivery device 104 to the rim portion 120 of the sheath. In the example shown, the holes 150 are equally spaced about the rim portion 120, thus allowing the pins 144 to be received at any two consecutive holes 150 around the rim portion 120. Other mechanisms for attaching the hub 142 to the sheath 102 may also be contemplated.

Figure 2:
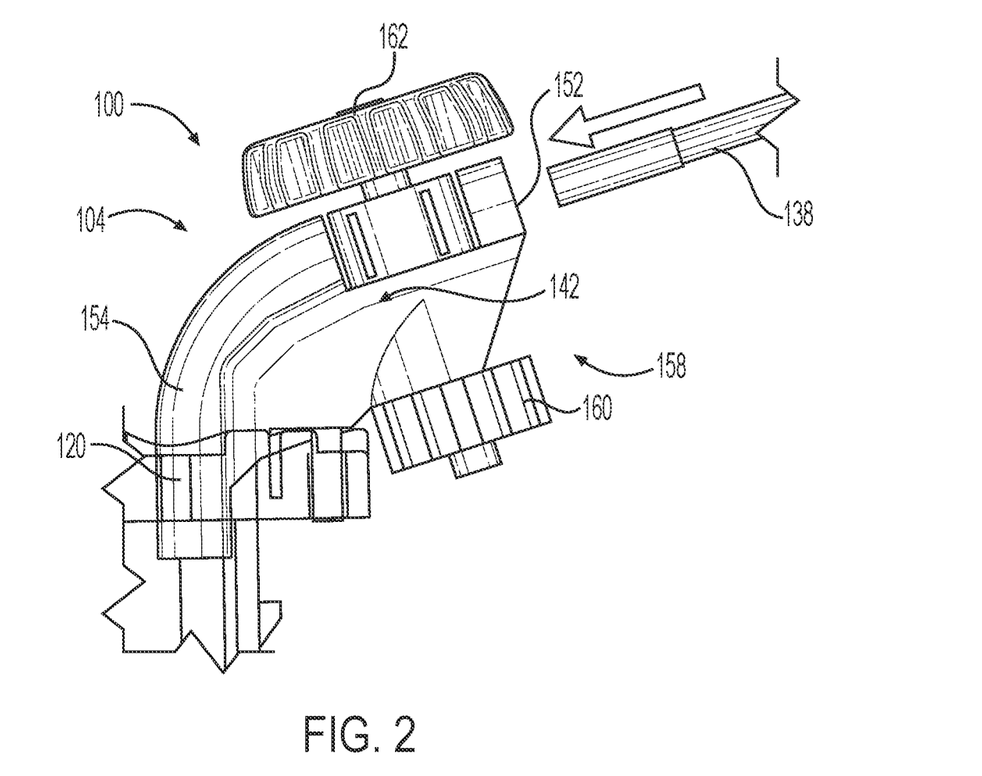
FIG. 2 illustrates a partial side view of the surgical access assembly of FIG. 1 with a guide tube in an uninstalled position.
Figure 3:
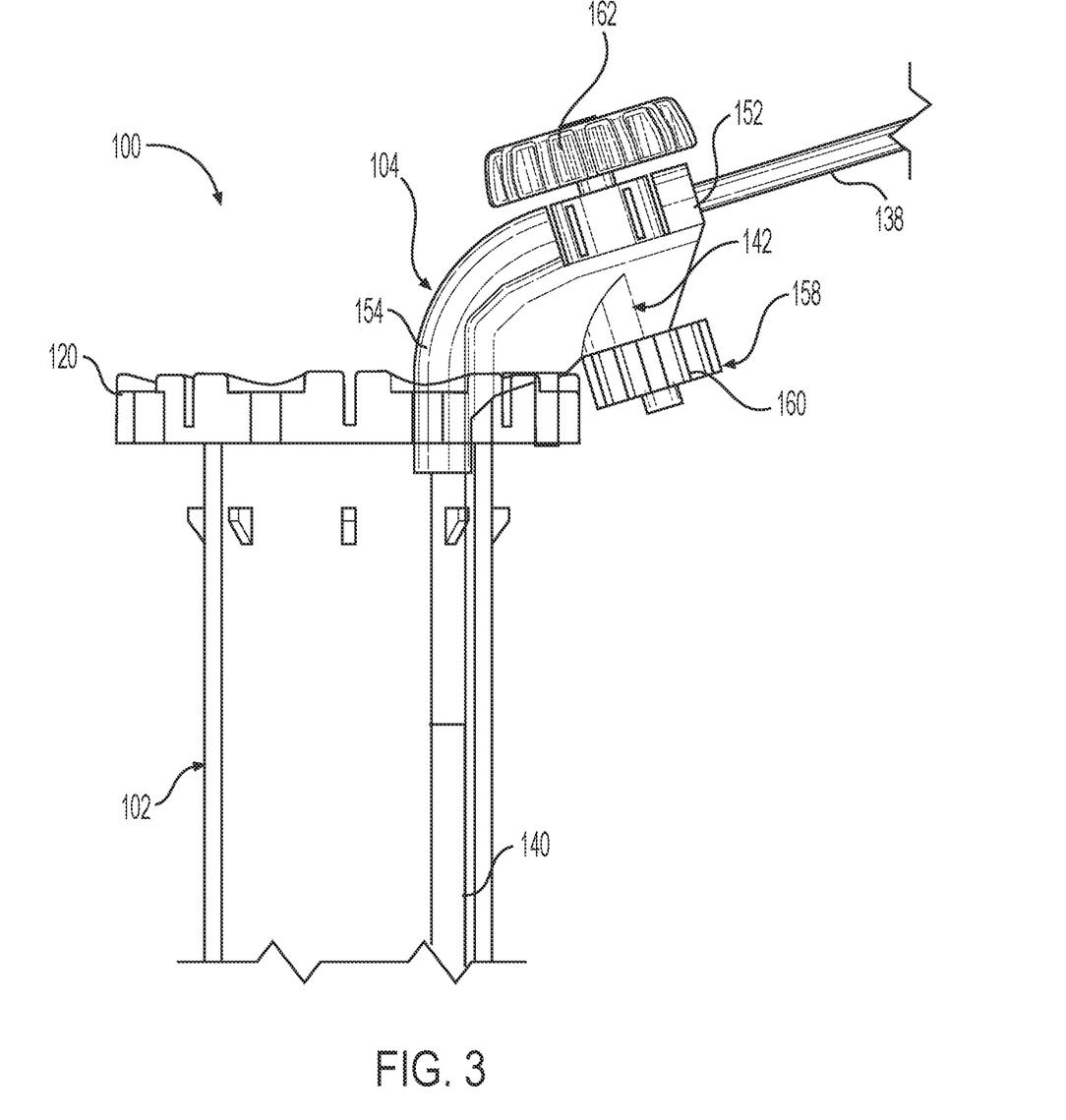
FIG. 3 illustrates a partial side view of the surgical access assembly of FIG. 1 with a guide tube in an installed position.

As best seen in FIGS. 1, 2, 3, 5, and 7, the hub 142 of the flexible tool delivery device 104 may define an aperture 152 configured to receive a tool 138. FIG. 2 illustrates a partial side view of the surgical access assembly 100 of FIG. 1 with the tool 138 in an uninstalled position where the flexible tool 138 has not yet been inserted into the aperture 152. FIG. 3, on the other hand, illustrates a partial side view of the surgical access assembly of FIG. 1 with the flexible tool 138 in an installed position. As explained above, the tool 138 may include any number of surgical tools including but not limited to a camera assembly, laser, fiberoptic device, resection device, biopsy device, wand, suction device, etc.

The tool 138 may be inserted into aperture 152 and received by a channel 154 defined by the hub 142. The channel 154 may be curved so as to guide the tool 138 downward into the guide tube 140. For this purpose, the tool 138 may be made of a bendable or malleable material such that the tool 138 may bend to conform to the curve of the channel 154, but also maintain a relatively straight form when extending through the guide tube 140 and into the sheath 102.

Once inserted into the aperture 152, the tool 138 may be selectively driven into the lumen of the outer sheath 102. In the example shown, the tool 138 may be fed through the aperture by a gear set 158. The channel 154 guide the tool 138 into the guide tube 140. The gear set 158 may move the tool 138 into the guide tube 140, towards the distal end 108 of the sheath 102 or retract the tool 138 away from the distal end 108.

Figure 4:
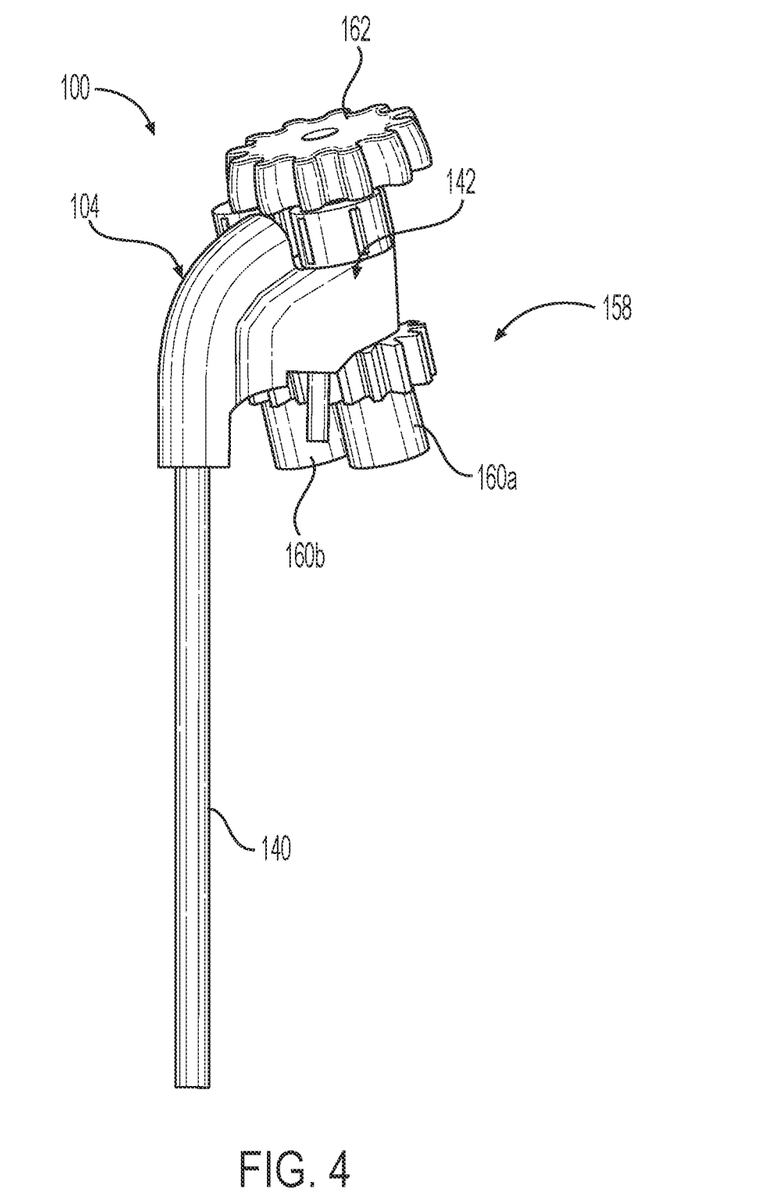
FIG. 4 illustrates a rear perspective view of the flexible instrument of FIG. 1.
Figure 5:
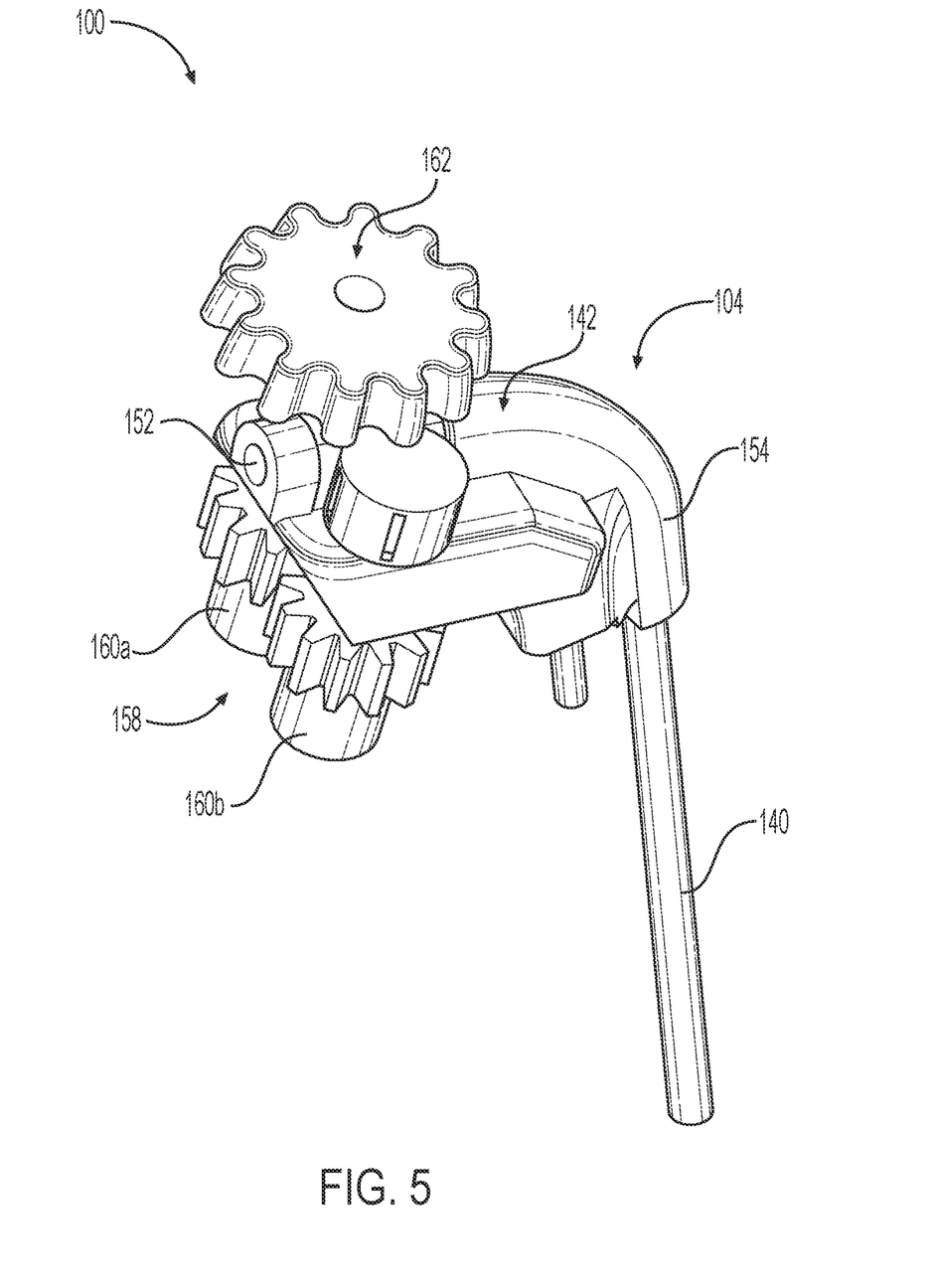
FIG. 5 illustrates a perspective front view of the flexible instrument of FIG. 1.

Referring to the figures, including FIGS. 4 and 5, the gear set 158 may include a pair of gears 160 configured to interlock with one another and rotate in opposite directions. That is, as a first gear 160a rotates clockwise, the other second gear 160b rotates in a reciprocal direction, or counterclockwise. The gear set 158 may be controlled by a control knob 162. The control knob 162 may be arranged at a top or upper side of the hub 142 and may be configured to selectively rotate the gears of the gear set 158. A drive wheel 164 may be coupled to the control knob 162 as well as the first gear 160a. When the drive wheel 164 rotates in a first direction, so does the drive wheel 164 and the first gear 160a.

Similarly, a follow wheel 166 may be coupled to the second gear 160b and configured to rotate with the second gear 160b. the second gear 160b may rotate upon rotation of the first gear 160a. Thus, when the first gear 160a and the drive wheel 164 are rotated by the control knob 162, the second gear 160b, as well as the follow wheel 166, are also rotated. Thus, the drive wheel 164 and follow wheel 166 are both driven the by the control knob 162.

The drive wheel 164 and follow wheel 166 may be cylinders. The drive wheel 164 and the follow wheel 166 are fixed on either side of the channel 154 and are configured to engage with the tool 138. That is, the drive wheel 164 and follow when 166 may "pinch" the tool 138. Consequently, when the drive wheel 164 and follow wheel 164 rotate, the tool 138 may be translated in that direction. The drive wheel 164 and follow wheel 166 may also maintain or hold the tool 138 at a fixed position once a desired location of the tool 138 has been reached. The drive wheel 164 and the follow wheel 166 may be made of silicone or a similar material having some compliance in order to accommodate varying diameters of the flexible tool 138.

Figure 6:
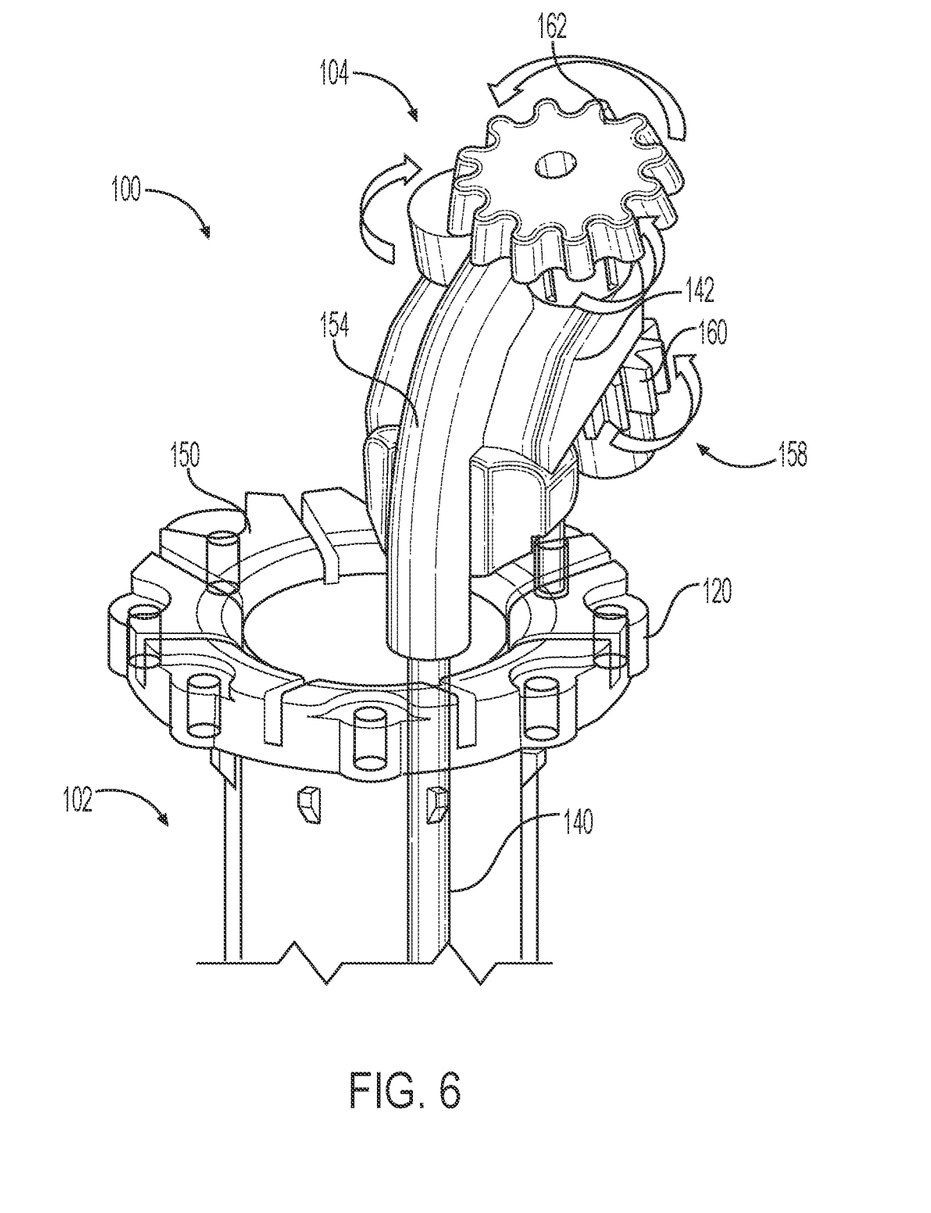
FIG. 6 illustrates a partial perspective front view of the surgical access assembly of FIG. 1 with a gear system moving in a first movement.
Figure 7:
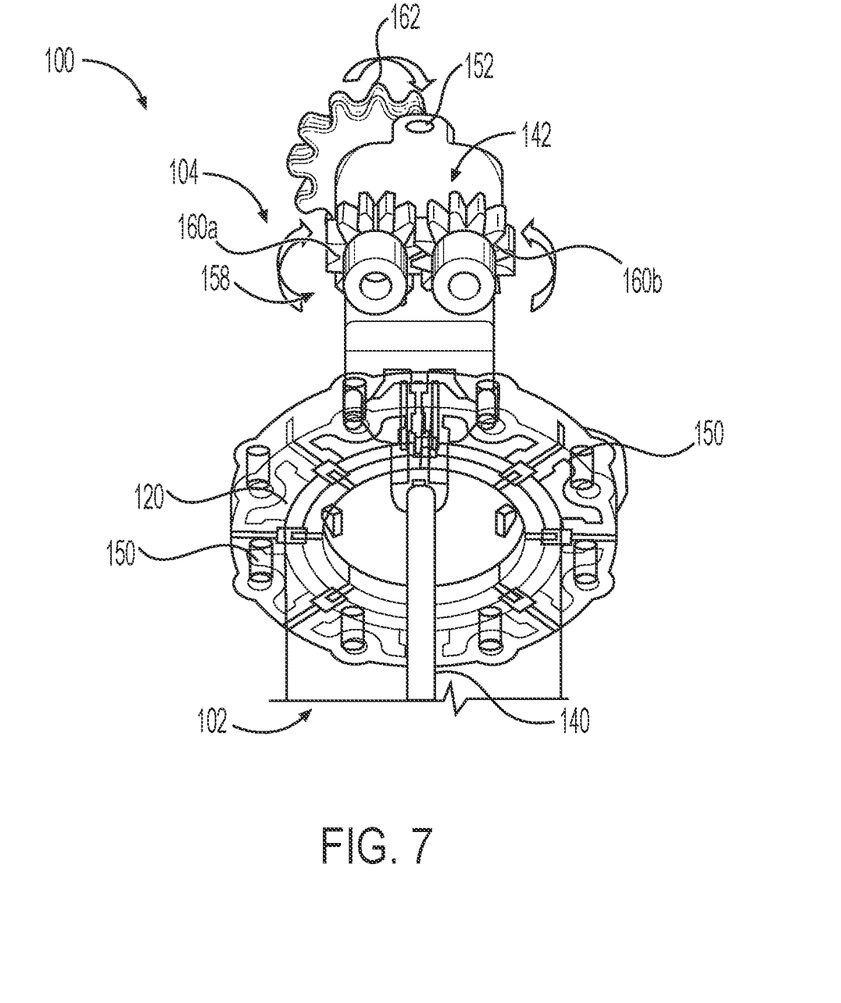
FIG. 7 illustrates a partial perspective rear view of the surgical access assembly of FIG. 6.

Referring specifically to FIGS. 6 and 7, where FIG. 6 illustrates a partial perspective front view and FIG. 7 illustrates a partial perspective rear view of the surgical access assembly 100 with the gear system 158 moving in a first movement. In this example, a counterclockwise rotation of the control knob 162 may cause gears to rotate towards one another and the tool 110 to move into the guide tube 140 within sheath 102 towards the distal end thereof.

A counterclockwise motion, or second movement, may reverse the direction of the gears 160, causing each to rotate away from each other, causing tool 138 to retract and move away from the distal end 108 of the sheath 102. Accordingly, by rotating the control knob 162, the length of the position of the tool 138 relative to the sheath 102 may be adjusted. The control knob 162 may include projections and define ridges configured to allow for easy actuation or rotation by the user. In one example, a surgeon's thumb may rotate the knob 162 in a clockwise or counterclockwise direction so as to adjust the position of the distal end of the flexible tool 138 within the sheath 102. Because the hub 142 is arranged on a side of the sheath 102 as opposed to be arranged at the center or above the sheath 102, visibility down the sheath 102 is maintained.

As explained, an instrument or flexible tool 138 may be delivered through the guide tube 140. The instrument may include the camera and/or a light source to acquire images of the surgical site to permit visualization of tumors, vessels, fiber tracks, fascicles and even healthy tissue, in real-time. The camera may enable the surgeon to have real-time information about the fiber tract and fascicle location, after placement of outer sheath 102. The camera may also provide light at specific wavelengths to illuminate fluorescents within the tissue at the surgical site. In one example, the camera may be housed within the hub 142. The camera may be a fiberoptic camera having glass fibers configured to deliver light. The camera may be a CMOS camera located on the distal end of the tool 138. In other examples, the camera arranged within the hub. The camera could also be independent of the hub 142 and guide tube 140.

In addition to the length of the flexible tool 138 extending from the guide tube 140 within the sheath 102 being adjustable, the angle of the flexible tool 138 may also be adjustable. This may be achieved by pivoting the hub 142 at the rim portion 120 in order to adjust the relative angle of the tube 140 extending therefrom. This may allow the surgeon to easily adjust the light source and/or camera without the need to reposition the outer sheath 102, avoiding unnecessary intrusion and trauma to the nearby tissue.

While the guide tube 140 is discussed herein, the hub 142 itself may deliver the tool to the proximal end of the sheath without the use of the guide tube 140. For example, the hub 142 may be configured to receive a camera and angle the camera down the sheath 102 to image the tissue proximal to the distal end of the sheath 102. Thus, the flexible tool may be delivered to the tissue.

Figure 8:
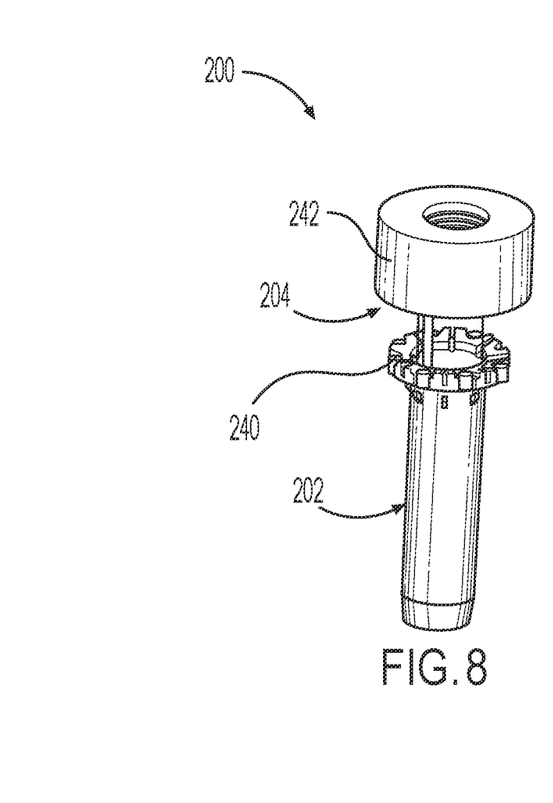
FIG. 8 illustrates a perspective view of another surgical access assembly.

FIG. 8 illustrates a perspective view of another surgical access assembly 200. This example assembly 200 may include a sheath 202 and a hub 242 maintaining a guide tube 240. Depth markings may be included to aid in identifying the relative position of the tube 240 within the sheath 202.

Figure 9:
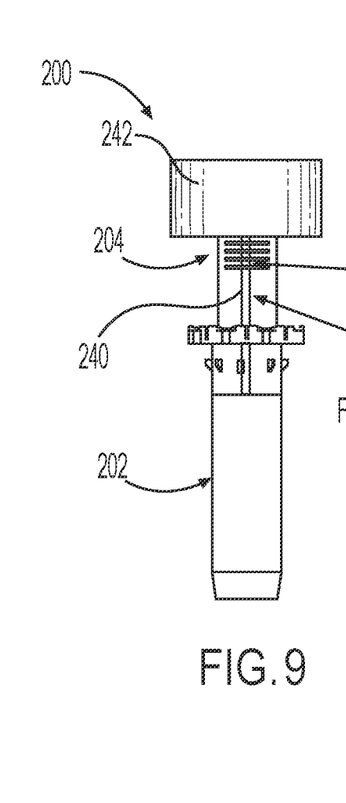
FIG. 9 illustrates a side view of the surgical access assembly of FIG. 8 in a first position.
Figure 10:
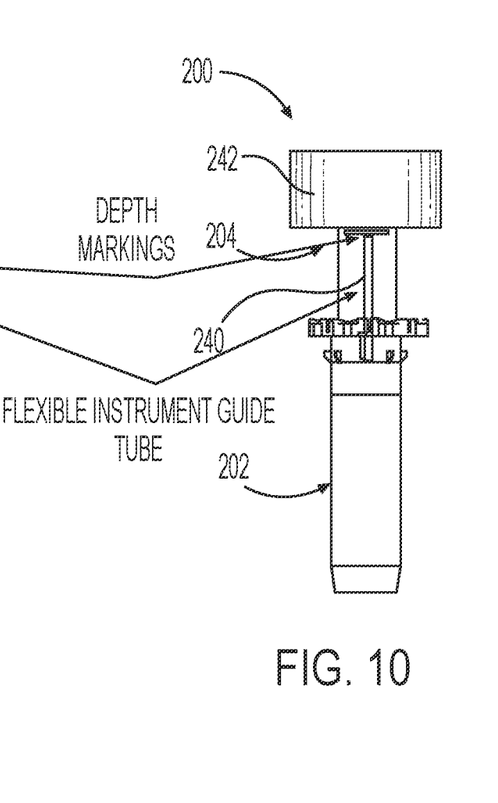
FIG. 10 illustrates a side view of the surgical access assembly of FIG. 8 in a second position.
Figure 11:
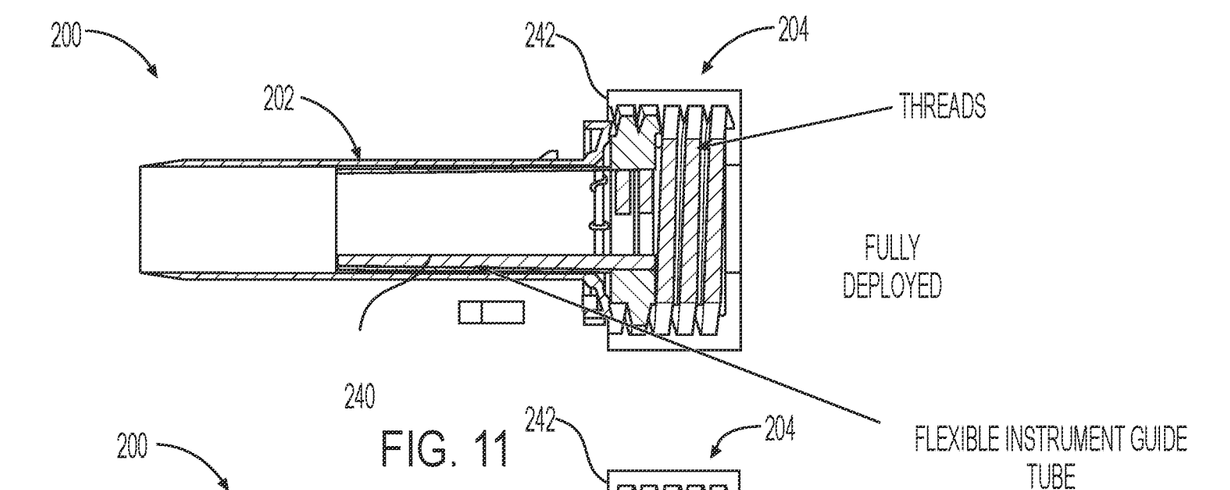
FIG. 11 illustrates a cut-away view of the surgical access assembly of FIG. 9.
Figure 12:
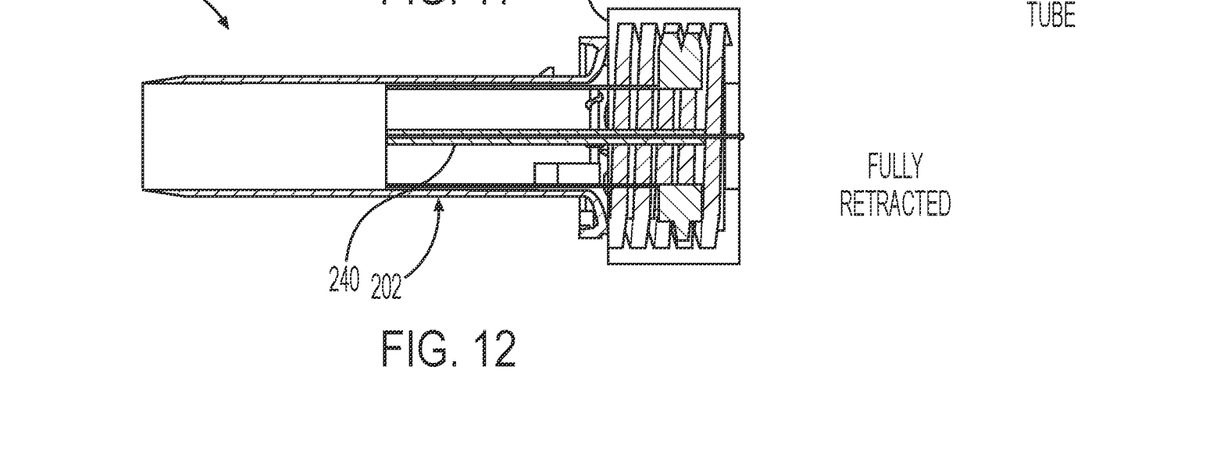
FIG. 12 illustrates a cut-away view of the surgical access assembly of FIG. 10.

FIG. 9 illustrates a side view of the surgical access assembly 200 of FIG. 8 in a first position while FIG. 10 illustrates a side view of the surgical access assembly 200 of FIG. 8 in a second position. FIG. 11 illustrates a cut-away view of the surgical access assembly 200 of FIG. 9 and FIG. 12 illustrates a cut-away view of the surgical access assembly 200 of FIG. 10.

Figure 13:
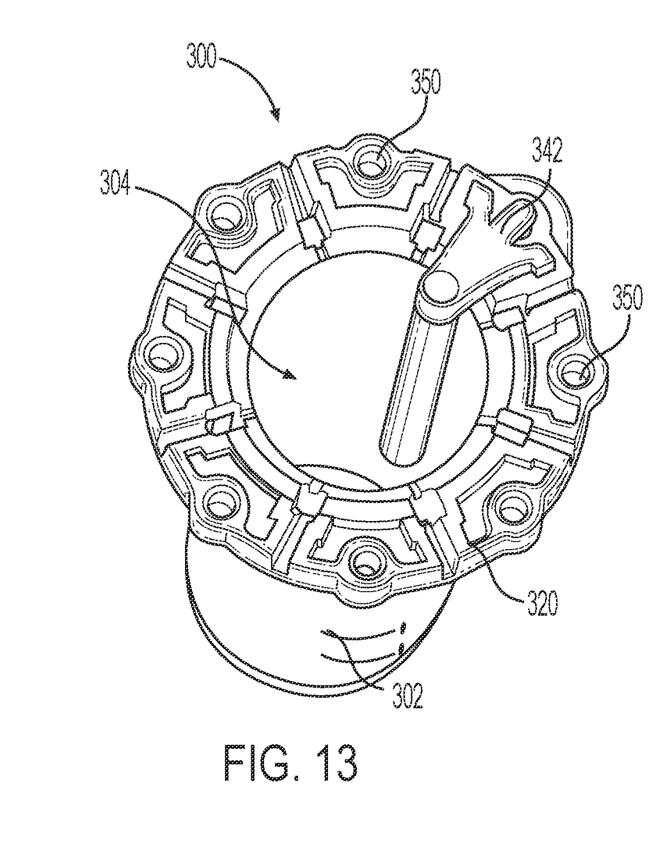
FIG. 13 illustrates a perspective view of another surgical access assembly.

FIG. 13 illustrates a perspective view of another surgical access assembly 300 having a flexible instrument 304 arranged on a hollow outer sheath 302. A rim portion 320 is configured as a ring, as illustrated in the drawings. The rim portion 320 may be configured as a grip portion, allowing for engagement by the surgeon as well as configured to receive a hub 342 of the flexible instrument 304, similar to the example shown in FIG. 1. As explained, the flexible instrument 304 may include a guide tube 140 extending down into the outer sheath, without substantially filling or blocking the lumen of the sheath 102.

Figure 14:
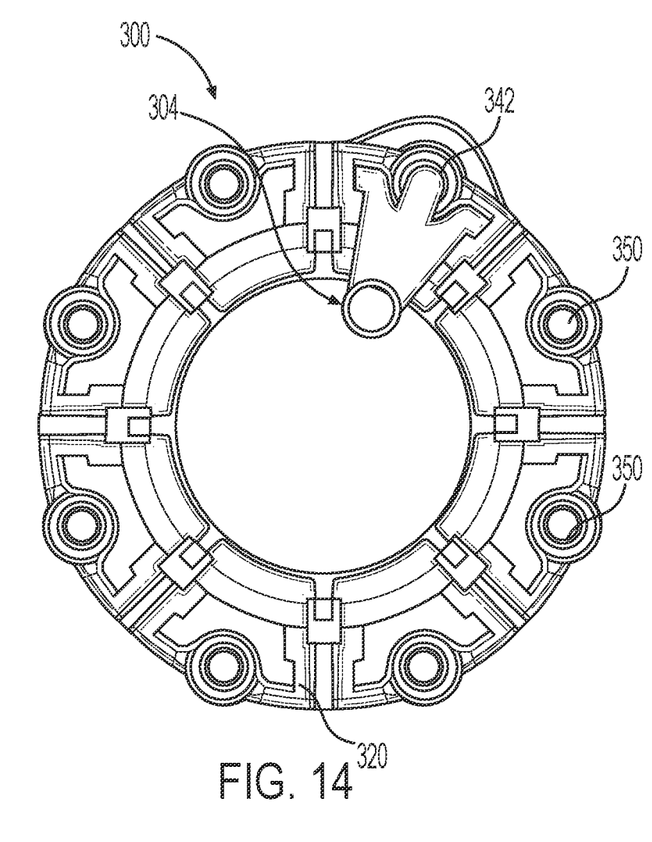
FIG. 14 illustrates a top view of the surgical access assembly of FIG. 13.
Figure 15:
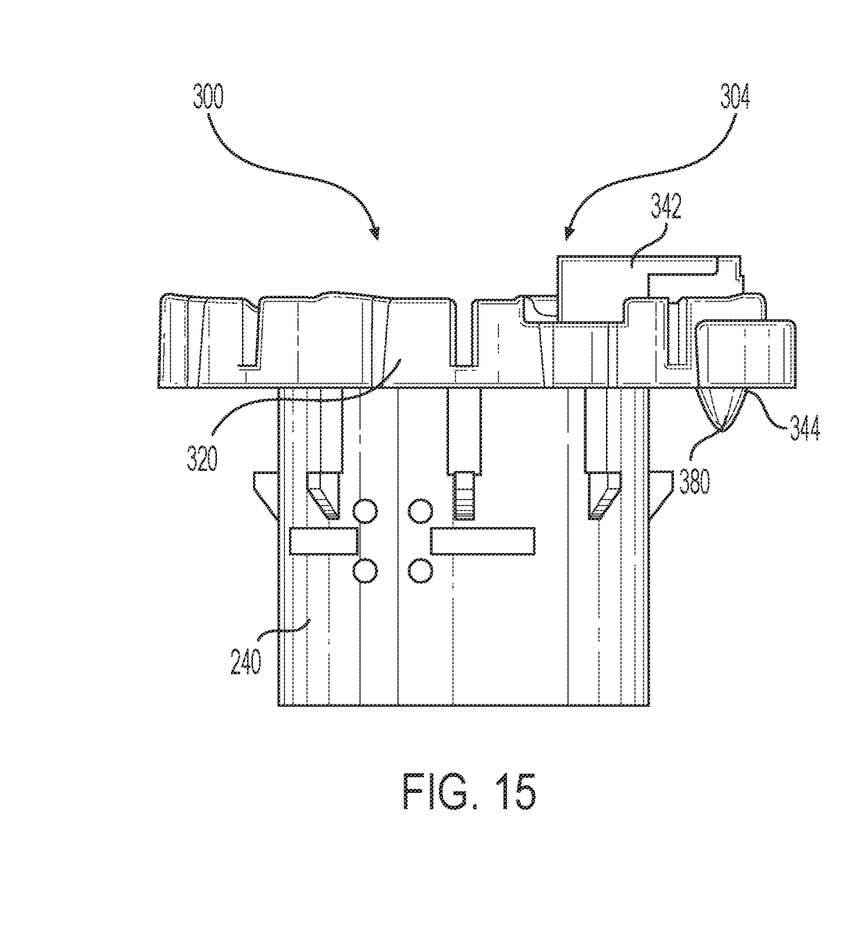
FIG. 15 illustrates a side view of the surgical access assembly of FIG. 13.
Figure 16:
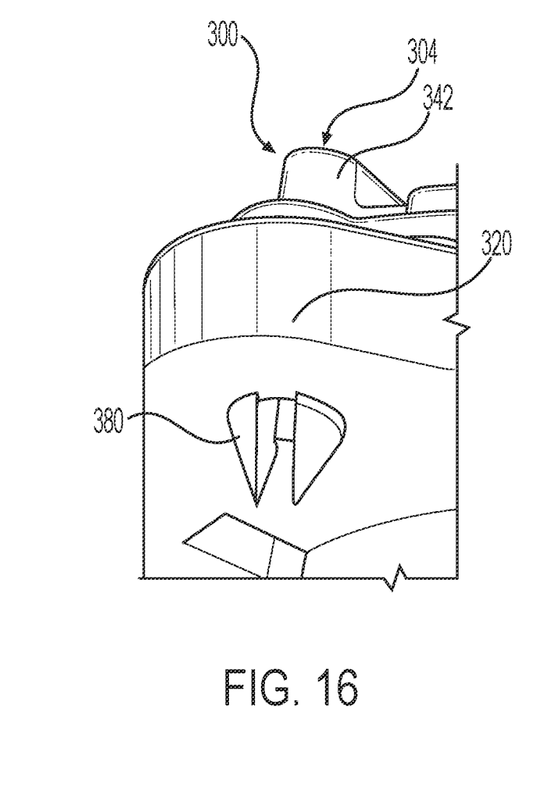
FIG. 16 illustrates a perspective bottom view of the surgical access assembly of FIG. 13.

Referring also to FIGS. 14, 15 and 16, the flexible instrument 304 includes the hub 342 configured to rest at the rim portion 320. The hub 142 may selectively secure onto the rim portion 320 via a plurality of mechanisms. In the example shown, the hub 342 may include at least one projection 344, as best illustrated in FIG. 15. The at least one projection 344 may include a pair of projections arranged on each side of a body of the hub 342. A plurality of equally spaced holes 350 defined along the rim portion 320 may be configured to receive the at least one projection 344 and secure the flexible instrument 304 to the rim portion 320 of the sheath 302. As explained, in the example shown, the holes 350 are equally spaced about the rim portion 320, thus allowing the pins 144 to be received at any two consecutive holes 150 around the rim portion 120. Other mechanisms for attaching the hub 142 to the sheath 102 may also be contemplated.

The projections 344 may include a distal end 380 configured to be snap-fit through the holes 350. The distal end 380 may include a malleable pair of cones configured to be forced together upon insertion into the hole 350, and then biased outwardly back to their resting position once the projection 344 has proceeding through the hole 350 to snap fit the projection within the hole 350. The distal end 380 may, additionally or alternatively, include a bolt, or other securing mechanism, to aid in maintaining the projections 344 within the holes 350.

It will be appreciated that the surgical access system and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this disclosure have been explained and illustrated in exemplary embodiments.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the disclosure should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A surgical access assembly, comprising
an outer sheath defined by an open distal end and an open proximal end and including a hollow body portion therebetween; and
a flexible tool delivery device having a hub and a guide tube, the hub configured to selectively secure to a rim at the proximal end of the outer sheath, and the guide tube configured to extend at least partially into the outer sheath and provide a flexible tool proximate to a tissue, wherein the hub includes at least one pin and wherein the rim defines at least one hole configured to receive the pin of the hub to secure the hub to the sheath.

2. The assembly of claim 1, wherein the hub is configured to receive the flexible tool and provide the flexible tool to the guide tube.

3. The assembly of claim 2, wherein the hub includes a pair of wheels configured to receive the flexible tool therebetween and drive the flexible into and out of the guide tube.

4. The assembly of claim 3, wherein the hub includes at least one control knob configured to selectively rotate the wheels such that the flexible tool is frictionally engaged between the wheels to as to be guided into the guide tube towards the distal end of the guide tube when the control knob is rotated in a first direction, and where the flexible tool is retracted in the opposite direction towards a proximal end of the guide tube when the control knob is rotated in an opposite second direction.

5. The assembly of claim 3, wherein the wheels are mailable and configured to receive flexible tools with varying diameters.

6. The assembly of claim 3, wherein the hub includes a channel connected to the guide tube and configured to receive the flexible tool, the wheels are arranged on each side of the channel such that the flexible tool is movable within the channel and guide tube.

7. The assembly of claim 1, wherein the hub is pivotable at the rim of the sheath such that the angle of the guide tube is selectively adjustable based on the relative angle of the hub with respect to the sheath.

8. The assembly of claim 1, wherein the pin includes a projection at a distal end of the pin configured to snap fit within the hole.

9. The assembly of claim 1, wherein the hub includes at least two pins and wherein the rim defines a plurality of equally spaced holes configured to receive the pins of the hub to secure the hub to the sheath.

10. A flexible tool delivery device for a surgical system, comprising
a hub configured to selectively secure to a rim at a proximal end of an outer sheath of the surgical system, and
a guide tube coupled to the hub and extending at least partially into the outer sheath to provide a flexible tool proximate to a tissue during use, wherein the hub includes at least one pin and wherein the rim defines at least one hole configured to receive the pin of the hub to secure the hub to the sheath.

11. The flexible tool delivery device of claim 10, wherein the hub is configured to receive the flexible tool and provide the flexible tool to the guide tube.

12. The flexible tool delivery device of claim 11, wherein the hub includes a pair of wheels configured to receive the flexible tool therebetween and drive the flexible tool into and out of the guide tube.

13. A flexible tool delivery device for a surgical system, comprising
a hub configured to selectively secure to a rim at a proximal end of an outer sheath of the surgical system, and
a guide tube coupled to the hub and extending at least partially into the outer sheath to provide a flexible tool proximate to a tissue during use,
wherein the hub is configured to receive the flexible tool and provide the flexible tool to the guide tube,
wherein the hub includes a pair of wheels configured to receive the flexible tool therebetween and drive the flexible tool into and out of the guide tube, and
wherein the hub includes at least one control knob configured to selectively rotate the wheels such that the flexible tool is frictionally engaged between the wheels to as to be guided into the guide tube towards the distal end of the guide tube when the control knob is rotated in a first direction, and where the flexible tool is retracted in the opposite direction towards a proximal end of the guide tube when the control knob is rotated in an opposite second direction.

14. The flexible tool delivery device of claim 12, wherein the wheels are mailable and configured to receive flexible tools with varying diameters.

15. The flexible tool delivery device of claim 12, wherein the hub includes a channel connected to the guide tube and configured to receive the flexible tool, the wheels are arranged on each side of the channel such that the flexible tool is movable within the channel and guide tube.

16. The flexible tool delivery device of claim 10, wherein the hub is pivotable at the rim of the sheath such that the angle of the guide tube is selectively adjustable based on the relative angle of the hub with respect to the sheath.

17. A surgical access assembly, comprising
an outer sheath defined by an open distal end and an open proximal end and including a hollow body portion therebetween; and
a flexible tool delivery device having a hub configured to selectively secure to a rim at the proximal end of the outer sheath and selectively receive a flexible tool to deliver the flexible tool, proximate to a tissue at a distal end of the outer sheath, wherein the hub includes at least one pin and wherein the rim defines at least one hole configured to receive the pin of the hub to secure the hub to the sheath.

18. A surgical access assembly, comprising
an outer sheath defined by an open distal end and an open proximal end and including a hollow body portion therebetween; and
a flexible tool delivery device having a hub and a guide tube, the hub configured to selectively secure to a rim at the proximal end of the outer sheath, and the guide tube configured to extend at least partially into the outer sheath and provide a flexible tool proximate to a tissue,
wherein the hub is configured to receive the flexible tool and provide the flexible tool to the guide tube,
wherein the hub includes a pair of wheels configured to receive the flexible tool therebetween and drive the flexible into and out of the guide tube, and
wherein the hub includes at least one control knob configured to selectively rotate the wheels such that the flexible tool is frictionally engaged between the wheels to as to be guided into the guide tube towards the distal end of the guide tube when the control knob is rotated in a first direction, and where the flexible tool is retracted in the opposite direction towards a proximal end of the guide tube when the control knob is rotated in an opposite second direction.

19. The assembly of claim 18, wherein the hub includes a gear assembly coupled to the control knob and configured to rotate the wheels in response to rotation of the control knob.

20. The flexible tool delivery device of claim 13, wherein the hub includes a gear assembly coupled to the control knob and configured to rotate the wheels in response to rotation of the control knob.

21. The flexible tool delivery device of claim 12, wherein the hub includes at least one control knob configured to selectively rotate the wheels such that the flexible tool is frictionally engaged between the wheels to as to be guided into the guide tube towards the distal end of the guide tube when the control knob is rotated in a first direction, and where the flexible tool is retracted in the opposite direction towards a proximal end of the guide tube when the control knob is rotated in an opposite second direction.

22. A flexible tool delivery device for a surgical system, comprising
a hub configured to selectively secure to a rim at a proximal end of an outer sheath of the surgical system, and
a guide tube coupled to the hub and extending at least partially into the outer sheath to provide a flexible tool proximate to a tissue during use,
wherein the hub is configured to receive the flexible tool and provide the flexible tool to the guide tube,
wherein the hub includes a pair of wheels configured to receive the flexible tool therebetween and drive the flexible into and out of the guide tube, and
wherein the hub includes a channel connected to the guide tube and configured to receive the flexible tool, the wheels are arranged on each side of the channel such that the flexible tool is movable within the channel and guide tube.

* * * * *